United States Patent [19]

Miller et al.

[11] 4,206,221

[45] Jun. 3, 1980

[54] CEPHALOMANNINE AND ITS USE IN TREATING LEUKEMIC TUMORS

[75] Inventors: Roger W. Miller; Richard G. Powell, both of Peoria; Cecil R. Smith, Jr., Dunlap, all of Ill.

[73] Assignee: The United States of America as represented by the Secretary of Agriculture, Washington, D.C.

[21] Appl. No.: 739

[22] Filed: Jan. 3, 1979

[51] Int. Cl.$^2$ ............... C07D 305/14; A61K 31/335
[52] U.S. Cl. ................................. 424/278; 260/333
[58] Field of Search ..................... 260/333; 424/278

[56] References Cited
PUBLICATIONS

J. M. Kingsbury, Poisonous Plants of the United States and Canada (1964), pp. 121–123.
M. C. Wani et al., J. Amer. Chem. Soc., vol. 93 (1971), pp. 2325–2327.
D. K. Ferguson, Review of Palaeobotany and Palynology, vol. 26 (1978), pp. 213–226.
Cancer Research, Part 2, vol. 26, No. 3, Mar. 1966, pp. 218 and 348.

*Primary Examiner*—Norma S. Milestone

*Attorney, Agent, or Firm*—M. Howard Silverstein; David G. McConnell; Curtis P. Ribando

[57] ABSTRACT

A novel alkaloid named "cephalomannine" has been produced from the tissue of plants belonging to the group commonly known as taxads and has proven to be effective in causing the remission of leukemic tumors in mice treated therewith. Cephalomannine is characterized by the following structural formula:

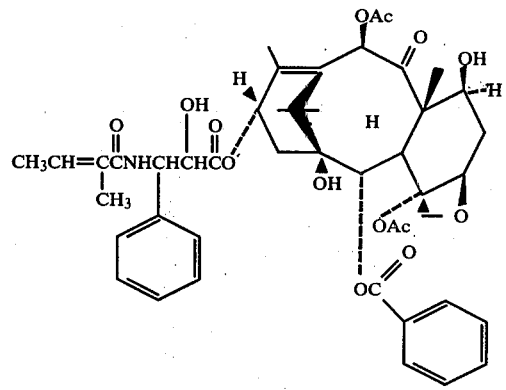

4 Claims, No Drawings

CEPHALOMANNINE AND ITS USE IN TREATING LEUKEMIC TUMORS

BACKGROUND OF THE INVENTION

1. Field of the Invention

This invention relates to a novel alkaloid compound which is useful as a chemotherapeutic agent for the remission of leukemia in animals.

2. Description of the Prior Art

The search for chemical compounds which are chemotherapeutically active against leukemia systems has revealed a series of cephalotaxine esters which are naturally occurring in the plant material of the Japanese plum yew, *Cephalotaxus harringtonia*. [Powell et al., Tetrahedron Lett. 4081(1969); Powell et al., Tetrahedron Lett. 815 (1970); Mikolajczak et al., Tetrahedron 28: 1995 (1972); Powell et al., J. Pharm. Sci. 61(8): 1227–1230 (August 1972); U.S. Pat. No. 3,793,454; and U.S. Pat. No. 3,870,727.] Two of the esters, harringtonine and homoharringtonine have been approved for preclinical evaluation at the National Cancer Institute. In addition, several synthetic esters of cephalotaxine possessing antileukemic activity have been prepared [Mikolajczak et al., J. Med. Chem. 20: 328–332 (1977)].

Another antileukemic and antitumor agent, taxol, has been isolated from the stem bark of the western yew, *Taxus brevifolia* [Wani et al., J. Amer. Chem. Soc., 93: 2325–2327 (1971)]. This was the first compound possessing the texane ring which has been shown to have any chemotherapeutic activity. Taxol is characterized by the following chemical structure:

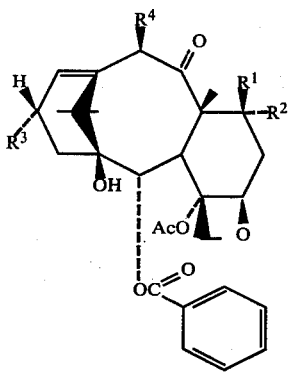

wherein
R$^1$=OH
R$^2$=H

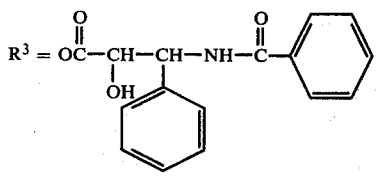

R$^4$=OAc

It is similar in structure to a series of related but inactive compounds, including:
baccatin III, wherein
R$^1$=OH, R$^2$=H, R$^3$=OH, R$^4$=OAc;
10-desacetyl baccatin III, wherein
R$^1$=OH, R$^2$=H, R$^3$=OH, R$^4$=OH;
baccatin V, wherein
R$^1$=H, R$^2$=OH, R$^3$=OH, R$^4$=OAc; and
10-desacetyl baccatin V, wherein
R$^1$=H, R$^2$=OH, R$^3$=OH, R$^4$=OH.

SUMMARY OF THE INVENTION

We have now surprisingly found a novel alkaloid compound which demonstrates activity against leukemia in animals, and has been given the name "cephalomannine." The compound is a taxane derivative characterized by the same ring structure as taxol and baccatin III, and distinguishes from them only in the C-13 ester functionality. Cephalomannine is characterized by the following structural formula:

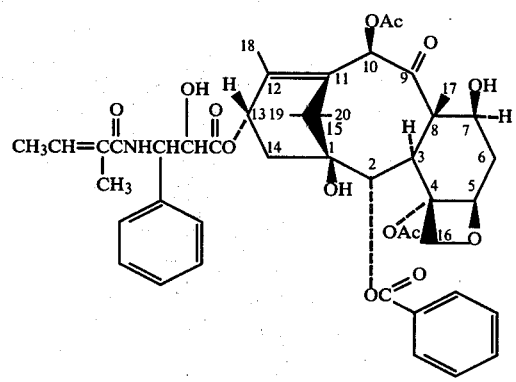

We have isolated this alkaloid from the plant material of a specimen belonging to the plant group of taxads. Members of this group are notorious for the extremely toxic compounds present in the plant tissue [J. M. Kingsbury, Poisonous Plants of the United States and Canada (1964), pp. 121–123]. Interfering agents, such as these toxic compounds, have the effect of masking the chemotherapeutic properties which we have discovered for the isolated product.

In accordance with this discovery, it is an object of the invention to introduce cephalomannine as a novel chemical compound having activity against leukemia.

Another object of the invention is to isolate cephalomannine in substantially pure form from taxad plant material containing the same.

It is also an object of the invention to administer the novel alkaloid compound to animals in order to cause remission of leukemia therein.

Other objects and advantages of the invention will become readily apparent from the ensuing description.

DETAILED DESCRIPTION OF THE INVENTION

The starting material for use in this invention is a plant material selected from the group of plants commonly referred to as taxads. While there is some disagreement among botanists as to the taxonomy of taxads [D. K. Ferguson et al., Review of Palaeobotany and Palynology 26: 213–226 (1978)], herein incorporated by reference, Ferguson has defined the group to include the genera Amentotaxus, Austrotaxus, Cephalotaxus, Pseudotaxus, Taxus, and Torreya. The most suitable plants of this group for use in the invention are those whose vegetative structures are most closely related macroscopically to *Cephalotaxus mannii*, *Taxus baccata*, and *Taxus wallichiana*, and particularly those which are also producers of the alkaloid taxol. A sample of such material has been deposited for purposes of comparison at the Northern Regional Research Center in Peoria, Ill., and has been assigned the Accession No. NU 52765. This sample was collected "in sterile" from a tree in the Shillong Forest in Assam, India, and has been identified by the collecting firm of Bhogilal C. Shah as being *Cephalotaxus mannii*. Others may designate it differently, such as belonging to the closely related and confusingly similar *Taxus wallichiana*, based upon the apparent absence of parenchyma in the secondary xylem of the woody tissue, the absence of resin canals in the leaf tissue, and upon the appearance of the cells around the stomates. However, despite the discrepancies in the taxonomy of taxads, the cephalomannine content of a particular species can be readily determined by HPLC and $^1$H n.m.r. analysis of a crude alkaloid extract as described below. While it is known that the subject compound can be extracted from the whole plant, it is presumed that separated parts such as the stems, roots, leaves, seeds, or mixtures thereof could also be used.

The plant material is first ground to a suitable particle size usually ranging from about 0.001 to about 10 mm.$^3$ This may be accomplished by serial passage through a chipper and a conventional grinding mill. The ground material is then extracted with a polar solvent such as an alcohol, preferably 95% ethanol. The solvent extract is separated from the solid residue and is concentrated to approximately 5% of its original volume. If the starting plant material included leaves, it is usually necessary to defat the concentrate by partitioning it between two immiscible solvents, one of which must be capable of dissolving the lipids in the leaves. For this purpose, water and a pentane-hexane mixture is desirable. The aqueous phase is separated from the lipid-containing fraction, and it is then extracted with choroform or an equivalent thereof. The chloroform phase is recovered from the extraction and constitutes the crude alkaloid extract.

Separation and purification of the cephalomannine could be accomplished by any conventional technique including countercurrent distribution (CCD), thin-layer chromatography (TLC), column chromatography (CC), high-pressure liquid chromatography (HPLC), or combinations thereof. We have successfully employed a series of operations comprising two serial passes on a silica column followed by two successive CCD's and finally HPLC. Other naturally-occurring alkaloids such as taxol and diterpenes such as baccatin III, which may be present in the extract, can also be isolated by this sequence.

EXAMPLE 1

ISOLATION OF CEPHALOMANNINE

Approximately 19 kg. of root, stem, and leaf material from the Accession No. NU 52765 sample were passed through a chipper and then ground in a Wiley mill to a particle size of about 0.001-10 mm.$^3$ The ground material was divided and each portion was extracted 5-7 times with 95% ethanol. The ethanol extracts were concentrated and combined into a 4477.9-g. sample, which was diluted with water to a volume of about 12 l. The aqueous ethanol extract was then extracted 4 times with petroleum ether (pentane-hexane) and 5 times with chloroform. The chloroform extracts were evaporated to dryness and combined for a total sample weight of 264 g. A 1.0397-g. assay sample of the dried extract was positive in both KB cell culture and in the PS leukemia system in mice.

The active chloroform extract was divided into eight 25-40 g. portions, each dissolved in 30-50 ml. of 5% methanol in chloroform. Each portion was passed through a first silica column (6 cm.×72 cm.) freshly packed with approximately 460 g. of silica prepared with chloroform. Two liters of 5% MeOH in CHCl$_3$ followed by 2 l. of 50% MeOH in CHCl$_3$ were passed through each column and collected in 32 fractions of 125 ml. each. After examination by TLC using 5% MeOH in CHCl$_3$, the 32 fractions from each run were combined into five, and similar fraction numbers from the eight runs were also combined. The resultant five fractions were assayed by KB cell culture and Fraction 3 (TLC: R$_F$ 0.3-0.6) proved to be the most active.

Sixty-seven grams of Fraction 3 were divided into nine 7-8 g. portions, each dissolved in 20 ml. of CHCl$_3$. Each portion was passed through a second silica column (4 cm.×70 cm.) freshly packed with approximately 240 g. of silica prepared with chloroform. The samples were eluted with a series of solvent systems including 1100 ml. of CHCl$_3$, 800 ml. of 2% MeOH in CHCl$_3$, 800 ml. of 5% MeOH in CHCl$_3$, 200 ml. of 100% MeOH, and 600 ml. of 50% MeOH in CHCl$_3$, respectively. After examination by TLC using 5% MeOH in CHCl$_3$, the 50 fractions collected from each run were combined into six, and similar fraction numbers from the nine runs were also recombined. The resultant six fractions were assayed by KB cell culture and Fraction 5 totaling 31 g. was the most active.

Fraction 5 was then passed through a first 200-tube CCD employing a four-component biphasic solvent system comprising ethyl acetate, hexane, methanol, and water in a 12:8:7:13 ratio, respectively. Eight hundred transfers of 40 ml./tube were made and 600 fractions were collected. After examination of a weight distribution curve based upon every tenth fraction, fractions were combined and assayed for activity by KB cell culture.

The most active fraction represented by transfer numbers 190-230 was recovered from the solvent and passed through a second CCD employing ethyl acetate, hexane, methanol, and water in a ratio of 12:18:13:7, respectively. After 600 transfers and analysis of every tenth fraction by weight distribution and TLC, fractions 100-200 were replaced with fresh upper and lower phase and the CCD instrument was set to recycle for a total of 600 additional transfers. Based upon the weight distribution of every tenth tube in the fundamental series, the 200 fractions were combined into 13 and assayed for activity. The fraction representing transfer tubes 70-90 and totaling 770 mg. was most active.

A total of 368 mg. of the above sample in 10% solution of 1:1 CHCl$_3$:MeOH was injected in 10-mg. increments into a HPLC column (C$_{18}$ μ bondapak, 3.9 cm.×30 cm.) set at a flow rate of 4 ml./min. of 60% MeOH in water solvent. Four fractions were collected, evaporated to dryness, and assayed. Fraction 3 (labeled K263) which came off at about 19.5 min. and Fraction 4 (labeled K264) which came off at about 23 min. showed activity. The compound comprising Fraction 4 was identified as taxol, and that of Fraction 3 was given the name "cephalomannine." Crystallization of Fraction 3 from aqueous methanol gave needles having the following properties: m.p. of 184°-186° C.; $[\alpha]_D$ —41° (MeOH), FDMS indicating an apparent M$^+$ at m/e 831 (7%) consistent with C$_{45}$H$_{53}$NO$_{14}$.

CHARACTERIZATION OF CEPHALOMANNINE STRUCTURE

The ring structure of cephalomannine has been ascertained by comparison with the known ring structure properties of taxol and baccatin III as reported in the literature. The $^1$H n.m.r. signals for these three compounds are shown in Table I below. The signals are all similar except for an upfield shift of the C-13 proton signal ($\delta$ 6.17 to 4.85) for baccatin III due to the absence of the nitrogen-containing ester grouping. Treatment of baccatin III with 1% sodium bicarbonate in methanol-water (3:1) at 26° C. for 5 hr. yields significant amounts of the 10-desacetyl baccatin III along with lesser amounts of baccatin V and 10-desacetyl baccatin V. Under identical conditions, cephalomannine yields a mixture including the same derivatives together with the methyl ester of the C-13 side chain, namely:

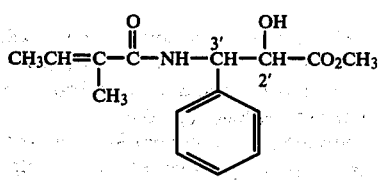

Thus, it is evident that cephalomannine and baccatin III share the same ring structure and that cephalomannine is in fact a C-13 derivative of baccatin III. Similarly, it is known in the art that taxol is a C-13 derivative of baccatin III, and therefore the cephalomannine diterpene ring must also be the same as that of taxol.

The methyl ester of the C-13 side chain obtained by reacting cephalomannine with sodium methoxide in methanol under anhydrous conditions is characterized as follows: a melting point of 129°–132° C.; a mass spectroscopic analysis showing a peak at m/e 218.1168 which compares favorably to the calculated value of m/e 218.1155 for $C_{13}H_{16}NO_2$ (M+ -$CO_2CH_3$); infrared analysis values as shown below in Table II; and $^1$H n.m.r. values as shown below in Table III.

Table I $^1$H n.m.r. of Ring Structure ($\delta$ Units, J Values Given in Hz)

| Protons and assignments | Taxol[1] | Baccatin III[2] | Cephalomannine |
|---|---|---|---|
| C2-H | 5.68,d,J=6 | 5.62,d,J=7 | 5.62,d,J=7 |
| C3-H | 3.80,d,J=6 | 3.86,d,J=7 | 3.74,d,J=7 |
| C5-H | 4.92,d,J=10 | 4.99,q,J=4,10 | 4.87,q,J=2,10 |
| C7-H | — | 4.46,q,J=6,10.5 | 4.32 |
| C10-H | 6.28,s | 6.30,s | 6.23,s |
| C13-H | 6.20,br.t,J=8 | 4.85,m | 6.15,br.t,J=9 |
| C16-2H | 4.24,s | 4.17,d; 4.30,d,J=8[3] | 4.19,ABq,J=9 |
| C17-CH$_3$ | 1.14,s | 1.65,s[3] | 1.12,s |
| C18-CH$_3$ | 2.20,s | 2.25,s[3] | 2.20,s |
| C19-CH$_3$ | 1.22,s | 1.09,s[3] | 1.24,s |
| C20-CH$_3$ | 1.67,s | 1.09,s[3] | 1.65,s |
| C4-OAc | 1.80,s | — | 1.78,s |
| C10-OAc | 2.36,s | — | 2.32,s |

[1] Data reported by M. C. Wani et al., J. Amer. Chem. Soc. 93: 2325-2327 (1971).
[2] Data reported by D. P. Della Casa de Marcano et al., J.C.S. Chem. Comm., pp. 365-366 (1975); data translated from $\tau$ units to $\delta$ units.
[3] The correspondence between the numbering system used by D.P. Della Casa de Marcano et al. (left column) and that used herein (right column) is as follows:
C-20 C16
CH$_3$ on C-8 C17
CH$_3$ on C-12 C18
CH$_3$ on C-15$\beta$ C19
CH$_3$ on C-15$\alpha$ C20

Table II

| I.R.[1] for Methyl Ester of C-13 Side Chain | |
|---|---|
| Frequency (cm.$^{-1}$) | Chemical bond |
| 3480 | O—H or N—H |
| 3410 | O—H or N—H |
| 1710 | C=O (ester) |
| 1640 | C=O (amide) |
| 1605 | C=C |

[1] Sample in chloroform phase at 1% concentration in 1-mm. cell.

Table III $^1$H n.m.r. for Methyl Ester of C-13 Side Chain

| Number of protons | Assignment | $\delta$ | Multiplicity | Coupling constant J (Hz) |
|---|---|---|---|---|
| 3 | vinyl CH$_3$ | 1.72 | d | 7 |
| 3 | vinyl CH$_3$ | 1.82 | s | — |
| 3 | ester CH$_3$ | 3.78 | s | — |
| 1 | 2'H | 4.52 | d | 2 |
| 1 | 3'H | 5.54 | ABq | 2,8 |
| 1 | vinyl H | 6.48 | q | 7 |
| 1 | NH | 6.5 | d,br. | 8 |
| 5 | aromatic | 7.0-7.5 | m | |

CHEMOTHERAPEUTIC ACTIVITY

The chemotherapeutic activities of the fractions obtained in the isolation procedure may be determined by a KB Cell Culture Screen in accordance with the National Cancer Institute Protocol 1.600 [Geran et al., Cancer Chemother. Rep., Part 3, 3: 17 (1972)]. The results of this procedure are expressed as the dose that inhibits growth to 50% of control growth by 3 days after drug addition. Such a dose is referred to as ED 50 and activity is indicated for ED 50 levels of $\leq$30 $\mu$g./ml. The smaller the ED 50 level, the more active the test material. The activities of fractions K263 (cephalomannine) and K264 (taxol) obtained in Example 1 are reported below in Table IV.

Table IV

| Fraction | Alkaloid | ED 50 ($\mu$g./ml.) |
|---|---|---|
| K263 | cephalomannine | 3.8 × 10 (−3) |
| K264 | taxol | 1.2 × 10 (−3) |

The effectiveness of alkaloid compounds against lymphocytic leukemia cells of the strain P388 implanted in mice is another method of determining activity. These assays are made according to the National Cancer Institute Protocol 1.200 described in Geran et al. referred to above. The usefulness of cephalomannine as compared to taxol was ascertained by assaying Fractions K263 and K264 from Example 1 by this procedure. Starting 24 hr. after the tumor implantation, previously determined dosages of each compound were injected intraperitoneally once a day for 9 days. Survival time of treated leukemic mice is compared to that of untreated leukemic mice (T/C×100). A T/C value of 100% indicated no activity. A T/C value greater than 100% means that the treated mice are surviving longer than the control mice. A compound giving a T/C value greater than 125% is indicative of activity as defined by the NCI Protocols, above. The results are shown in Table V.

Table V

| Assay | Alkaloid | Dose mg./kg./inj.[1,2,3] | T/C,[4] % |
|---|---|---|---|
| A | cephalomannine | 3.30 | 180 |
| B | cephalomannine | 2.20 | 162 |
| C | cephalomannine | 1.40 | 159 |
| D | cephalomannine | 1.00 | 152 |
| E | taxol | 2.20 | 152 |
| F | taxol | 1.40 | 148 |

[1]All mice were female, DBA/2.
[2]The injection vehicle was saline + Tween 80 + alcohol.
[3]One intraperitoneal injection per day for 9 days.
[4]T/C = mean survival time of test animals/mean survival time of control animals; 125% or above considered active.

The terms "effective amount" and "effective dose" as referring to the treatment of animals is defined herein to mean those quantities of alkaloid which will cause remission of leukemia in the animal to which it is administered, without imparting a toxic response. The effective amount may vary with the injection vehicle, the injection schedule, the strain of leukemia, and other related factors, all of which may be varied without departing from the scope or operativeness of the invention. Generally an effective dose would be in the range of about 0.5–5.0 mg./kg. of body weight/day, and preferably in the range of about 1.0–3.3 mg./kg. of body weight/day.

It is understood that the foregoing detailed description is given merely by way of illustration and that modification and variations may be made therein without departing from the spirit and scope of the invention.

We claim:

1. A substantially pure chemotherapeutically active alkaloid compound cephalomannine having the following structure:

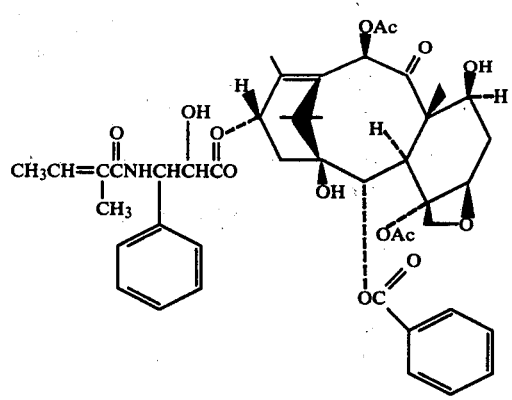

2. A chemotherapeutic composition suitable for the remission of leukemic tumors of the strain P388 comprising an injection vehicle and an effective amount of substantially pure cephalomannine.

3. The chemotherapeutic composition described in claim 2 wherein said injection vehicle is a liquid.

4. A method of treating animals for remission of leukemia of the strain P388 comprising administering to said animals a chemotherapeutic composition comprising an injection vehicle and an effective amount of substantially pure cephalomannine.

* * * * *